(12) United States Patent
Neftel (10) Patent No.: US 11,406,746 B2
(45) Date of Patent: Aug. 9, 2022

(54) USER INTERFACE FOR DIALYSIS TREATMENT

(71) Applicant: Debiotech S.A., Lausanne (CH)

(72) Inventor: Frédéric Neftel, Crans-Montana (CH)

(73) Assignee: Debiotech S.A., Lausanne (CH)

(*) Notice: Subject to any disclaimer, the term of this patent is extended or adjusted under 35 U.S.C. 154(b) by 568 days.

(21) Appl. No.: 15/527,335

(22) PCT Filed: Dec. 3, 2015

(86) PCT No.: PCT/IB2015/059317
§ 371 (c)(1),
(2) Date: May 17, 2017

(87) PCT Pub. No.: WO2016/088072
PCT Pub. Date: Jun. 9, 2016

(65) Prior Publication Data
US 2017/0361009 A1  Dec. 21, 2017

(30) Foreign Application Priority Data
Dec. 4, 2014 (WO) .................. PCT/IB2014/066597

(51) Int. Cl.
*A61M 1/28* (2006.01)
*G16H 40/63* (2018.01)
(Continued)

(52) U.S. Cl.
CPC .............. *A61M 1/282* (2014.02); *A61M 1/28* (2013.01); *G16H 20/17* (2018.01); *G16H 20/40* (2018.01);
(Continued)

(58) Field of Classification Search
CPC ........ A61M 1/28; A61M 1/282; A61M 1/284; A61M 2205/502; A61M 2205/505; G06F 19/3468
See application file for complete search history.

(56) References Cited

U.S. PATENT DOCUMENTS

2005/0256444 A1* 11/2005 O'Mahony ............. A61M 1/16
604/5.02
2008/0161751 A1* 7/2008 Plahey ................... G16H 20/40
604/29
(Continued)

FOREIGN PATENT DOCUMENTS

EP  1195171      4/2002
EP  2659918 A1   11/2013
(Continued)

OTHER PUBLICATIONS

European Application No. 15823771.9 Office Action dated Jun. 19, 2019.

*Primary Examiner* — Dung T Ulsh
(74) *Attorney, Agent, or Firm* — Andre Roland S.A.; Nikolaus Schibli (57) ABSTRACT

A graphical user interface for a medical system comprises a display device, an electronic processor that operates with the display device to display a plurality of screens including a programming screen by which a user can enter or modify medical treatment parameters employed by a machine to perform a medical treatment. When a user modifies a first medical treatment parameter, the processor is programmed to adjust at least one other medical treatment parameters depending on the first medical treatment parameters.

31 Claims, 7 Drawing Sheets

(51) Int. Cl.
*G16H 20/17* (2018.01)
*G16H 20/40* (2018.01)

(52) U.S. Cl.
CPC ....... *G16H 40/63* (2018.01); *A61M 2205/502* (2013.01); *A61M 2205/505* (2013.01)

(56) References Cited

U.S. PATENT DOCUMENTS

| | | | | |
|---|---|---|---|---|
| 2008/0172026 | A1* | 7/2008 | Blomquist | G16H 40/63 604/500 |
| 2010/0113891 | A1* | 5/2010 | Barrett | A61B 5/7275 600/301 |
| 2013/0184638 | A1* | 7/2013 | Scarpaci | A61M 1/3656 604/28 |
| 2013/0293570 | A1* | 11/2013 | Dolgos | A61M 1/16 345/619 |

FOREIGN PATENT DOCUMENTS

| | | |
|---|---|---|
| WO | WO 2010/108955 A1 | 9/2010 |
| WO | WO 2016/193930 A1 | 12/2016 |

\* cited by examiner

USER INTERFACE FOR DIALYSIS TREATMENT

CROSS REFERENCE TO RELATED APPLICATIONS

The present application is a U.S. national stage application of PCT/IB2015/059317 filed on Dec. 3, 2015 designating the United States, and claims foreign priority to International patent application PCT/IB2014/066597 filed on Dec. 4, 2014, the contents of both documents being herewith incorporated by reference in their entirety.

FIELD OF INVENTION

This invention relates to the field of medical instruments and their user interfaces, and more particularly to a user interface and control method for a medical instrument such as a dialysis machine.

STATE OF THE ART

Dialysis machines are used for treating patients with inadequate kidney function. Dialysis machines typically include, among other things, a dialysate circuit comprising a pump. When used for so-called peritoneal dialysis, said dialysate circuit is fluidly connected to the peritoneal cavity of a patient so that the dialysis machine infuses the dialysate into the patient's peritoneal cavity during a phase called fill phase, then the dialysate stays for a predetermined duration called dwell time during the so-called dwell phase, and after said predetermined duration the machine removes the dialysate from the peritoneal cavity during the so-called drain phase. Some machines are automatic in a manner to perform (during the night for example) an APD (Automated Peritoneal Dialysis).

Dialysis machines typically have a display device on which a plurality of so-called screens are displayed. By screen we understand a combination which may contain for example texts, images, graphs, graphics, movies, animations . . . . Some of these screens are used for programming the operation of the machine. Such screens in the past were rather unattractive and hard to use, and thus required complex manipulations and trained medical professionals to be used properly. The contemporary machines have a user interface allowing a patient or medical practitioner to interact with the machine and adjust machine operations or treatment parameters. But, most of these machines propose a complex programming sequence. Indeed, the user has to manually enter each parameter such as for example the volume of dialysate infused at each fill phase, the total volume of dialysate infused during the treatment, etc. . . . . And after each of such an entry, the user has to check and validate the entered parameter. Thus, it is fastidious and very long. Furthermore, in case of the user making a mistake, the machine of the art prompts the user to check, but the machine cannot adjust itself the data for such parameter.

The European Patent (EP1195171 B1, which is incorporated herein by reference) discloses a dialysis device comprising a display on a touch panel. Said device displays a still image and motion image so as to inform the patient about the dialysis treatment which is in progress. Said display arranges the information in such a way as to bring an inventive technical effect. But said technical effect is different from the present invention. Indeed, the data (more particular, the medical treatment parameters) are disposed in an ingenious way and/or are automatically adjusted in such a way as to prevent any mistake when the user programs the medical treatment.

GENERAL DESCRIPTION OF THE INVENTION

The present invention discloses a graphical user interface used in screens which is intuitive so that the user can program the dialysis machine more easily, without risk of error.

A first aspect of the invention provides a medical system for setting a medical treatment. This system comprises:
  a display device which comprises a graphical user interface. This graphical user interface is configured to display a first and a second parameter related to the medical treatment,
  a computing device operatively coupled to the display device. This computing device is configured to:
    display on the graphical user interface the first and the second parameter
    allow a user to modify the first and the second parameters; and
    when the first parameter has been modified by the user, adjust the second parameter and vice-versa.

A second aspect of the invention provides a dialysis system for performing a peritoneal dialysis treatment which comprises a cycle set which may comprise fill phase, dwell phase and/or drain phase. This system comprises:
  a display device which comprises a graphical user interface. This graphical user interface is configured to display a plurality of parameters on a setting screen. Preferentially, this setting screen comprises three distinct areas:
    a first area configured to depict a modifiable parameter related to the fill phase, the dwell phase or the drain phase,
    a second area configured to depict a modifiable parameter dedicated to the number of cycles, and
    a third area configured to depict a modifiable parameter dedicated to a dialysate volume or a duration of the treatment;
  a computing device operatively coupled to the display device, wherein the computing device is configured to:
    display on the graphical user interface the values of the parameters
    allow a user to modify at least one of the modifiable parameters; and
    when one of the modifiable parameters has been modified by the user, adjust at least one other parameter.

A third aspect of the invention provides a method which comprises:
  provision of a medical system for performing a medical treatment which comprises at least two distinct sets of cycles. Preferentially, each cycle set comprises at least one cycle and dedicated parameters;
  provision of a display device which comprises a graphical user interface; and
  displaying on the display device a plurality of stacked windows, Preferentially, each cycle set is displayed on a specific window and each window has a corresponding tab that is displayed on the user interface adjacent to the tabs of the other windows. Each tab is selectable (for example by a user) to bring the window corresponding to that tab to a top of the stack as an active window in which a user can view and/or edit parameters of the selected cycle set while the windows corresponding to the other tabs remain in the background.

A fourth aspect of the invention provides a method of setting parameter values in a peritoneal dialysis device. This method comprises:

Displaying on a graphical interface a plurality of parameters, one of the parameters being related to the drain phase, In response to a user selecting the parameters related to the drain phase, allowing the user to input a value to be assigned to the selected parameter Preferentially, the selected parameter is a percentage, which determines one of the following therapies:

A Tidal Peritoneal Dialysis, or

A Continuous Cycling Peritoneal Dialysis.

A fifth aspect of the invention provides a graphical user interface (GUI) for a medical system which comprises a display device, an electronic processor that operates with the display device to display a plurality of screens including a programming screen by which a user can enter or modify medical treatment parameters employed by a machine to perform a medical treatment. Said medical system is designed in such a way that, when a user modifies a first medical treatment parameter, the processor is programmed to adjust automatically at least one other medical treatment parameter depending on the first medical treatment parameter.

A sixth aspect of the invention provides a graphical user interface for a dialysis system which comprises a display device, an electronic processor that operates with the display device to display a plurality of screens including a cycle set programming screen by which a user can program a cycle set (for example a cycle set of a dialysis treatment comprising a fill phase, a dwell phase and an optional drain phase). Said cycle set programming screen may display a set of adjustable parameters used by the dialysis system in a dialysis treatment. When one of said adjustable parameters is changed by a user, the electronic processor automatically adjusts at least another adjustable parameter.

A seventh aspect of the invention provides a dialysis machine, which comprises a dialysate pump, a graphical user interface (GUI) and an electronic processor coupled to the pump and/or the GUI. The GUI allows a user to program a treatment comprising at least one cycle including at least one fill phase performed by the pump, at least one dwell phase and at least one drain phase performed by the pump. Preferentially, the GUI displays a graphic illustrating the three phases of one cycle and a set of adjustable parameters corresponding to the treatment. Advantageously, the processor and the GUI are adapted to adjust (and display said adjustment) at least one of said adjustable parameters when the user changes one of said adjustable parameters so that the dialysis machine offers an intuitive GUI.

An eighth aspect of the invention provides a graphical user interface (GUI) for a peritoneal dialysis system which comprises a display device, and an electronic processor that operates with the display device to display a programming screen adapted to program a treatment comprising a cycle including a fill phase, a dwell phase and an optional drain phase. Preferentially, said programming screen comprises three distinct areas:

a first area dedicated to the parameters of the fill phase, a second area dedicated to the parameters of the dwell phase, a third area dedicated to the parameters of the optional drain phase.

Optionally, one additional distinct area dedicated to other parameters of the treatment. Said other parameters may be the number of cycles to be conducted during the treatment and/or the total duration of the treatment and/or the total volume of dialysate used for the treatment. When one of said parameters is changed by a user, the electronic processor adjusts automatically at least one other parameters.

A ninth aspect of the invention provides a dialysis machine which has a graphical operator machine interface ("OMI") by which an operator is able to establish machine operating and dialysis treatment parameters employed by the dialysis machine in a dialysis treatment. Advantageously, the graphical OMI comprises:

a graphical screen by which to access, select, display and enter data;

a first area displaying a first predetermined group of dialysis treatment parameters used by the dialysis machine in a dialysis treatment;

a second area displaying a second predetermined group of dialysis treatment parameters used by the dialysis machine in a dialysis treatment;

a third area displaying a third predetermined group of dialysis treatment parameters used by the dialysis machine in a dialysis treatment;

an optional fourth area displaying a fourth predetermined group of dialysis treatment parameters used by the dialysis machine in a dialysis treatment.

Preferentially, at least one of the dialysis treatment parameters may be changed by the user. The dialysis machine may comprise an electronic processor and at least one mathematical model used by the processor. When the user changes one parameter, said mathematical model will be used to adjust at least one other parameter used by the dialysis machine in a dialysis treatment. Thanks to this mathematical model, the user has to validate only some dialysis treatment parameters and not each parameter.

A tenth aspect of the invention provides a method to assist a user in adjusting medical treatment parameters used by a medical device to perform a medical treatment, said method being employed by a device comprising a graphical user interface (GUI) connected to a processor, wherein said method comprises the following steps:

displaying on the GUI at least one of said medical treatment parameters, modifying one of said medical treatment parameters, adjusting automatically at least one another of said medical treatment parameters so that all parameters are consistent with the medical treatment.

An eleventh aspect of the invention provides a computer-implemented method adapted to assist an user in adjusting a medical treatment parameter which will be employed by a machine to perform a medical treatment, the computer-implemented method comprising:

Displaying a programming screen on a display device adapted to display visual information to the user, Detecting that the user has modified one of the medical treatment parameters, Adjusting automatically at least another medical treatment parameter so that all parameters are consistent with the treatment.

LIST OF FIGURES

The present invention will be better understood at the light of the following detailed description which contains non-limiting examples illustrated by the following figures.

LIST OF ELEMENTS 1 patient/user/caregiver . . .
2 cycler
3 cassette
4 supply bag
5 waste bag
6 processor
7 pumping mechanism
8 sensor
9,12 input means
10 display device
11 mathematical model
13 other means
20 cycle set programming screen
21 cycle which may be repeated in a manner as to form a cycle set
22 fill phase
23 dwell phase
24 drain phase
25, 26, 27a, 27b, 28, 29, 30 parameters
31, 32, 33, 34, 35, 36, 37 specific area of the cycle set programming screen
40 full treatment screen
41 a cycle
42 a first cycle set
43 a second cycle set
44 the tab of the full treatment screen
45 the tab of a cycle set programming screen
46 the tab of a cycle set programming screen
47 a validation icon
48 a setting icon
49 button
50 add button
51 delete button

DETAILED DESCRIPTION OF THE INVENTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, any direction referred to herein, such as "top", "bottom", "left", "right", "upper", "lower", and other directions or orientations are described herein for clarity in reference to the figures and are not intended to be limiting of an actual device or system. Devices and systems described herein may be used in a number of directions and orientations.

As used herein, "have", "having", "include", "including", "comprise", "comprising" or the like are used in their open ended sense, and generally mean "including, but not limited to".

As used in this specification and the appended claims, the term "or" is generally employed in its sense including "and/or" unless the content clearly dictates otherwise.

The invention discloses an intuitive setting means for a medical system. The medical system may be a machine by which a user can program all or parts of the parameters required to the medical treatment. Thus, said system may be a computer using software adapted to program the parameters required to the treatment and said system may comprises a medical device adapted to perform the medical treatment.

The system comprises a display device, input means and an electronic processor which controls the display device and the input means. Said inputs means may be a touch screen or a keypad, or a mouse or at least one button. Said input means may be adapted to access, select, activate, enter and/or modify a data which may be a parameter of the medical treatment.

The invention describes, among other things, an inventive graphical user interface which is an interface between the system and the user. Said interface displays some visual information to the user and allows the user to enter some data to the system. The GUI may comprise input means, a display device and a processor which cooperates with said elements. Said input means may be distinct from the display device. In other terms, the GUI is a device including several elements which may be distinct. In other case, if the GUI comprises a touch screen, then the user can enter some data through the display device.

Figure 1:
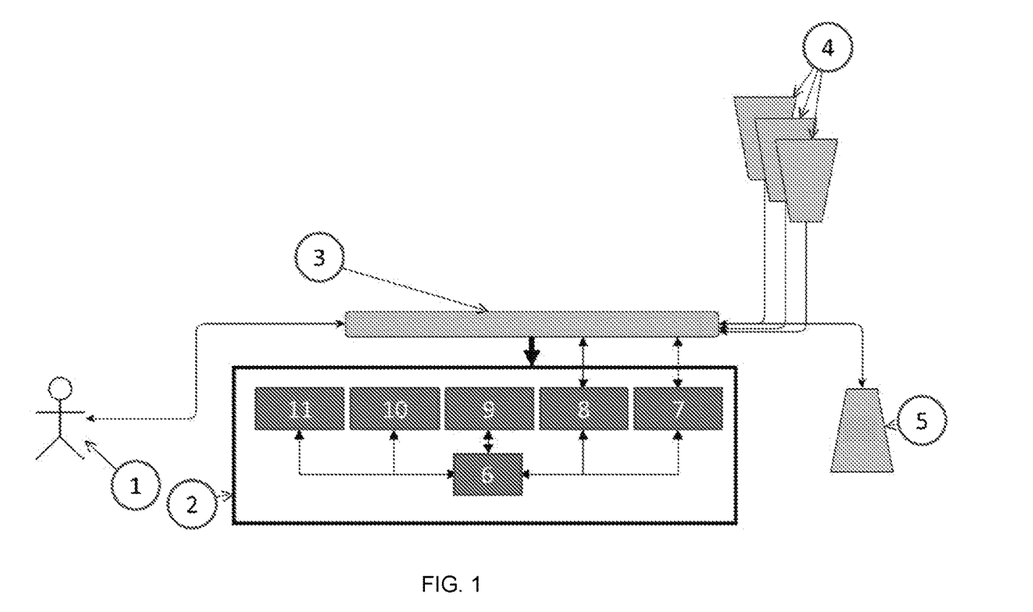
FIG. 1 illustrates a system which comprises a cycler

In the case where the system is a dialysis treatment system including a cycler, the system furthermore comprises a dialysate circuit, a pump and a bag which may store dialysate. The electronic processor may control also the pump. The dialysate circuit, the pump and the bag may be fluidly connected. The FIG. 1 illustrates such a system. In one embodiment, the system comprises a cycler (2) and a cassette (3) which is fluidly connected to at least one optional supply bag (4) and/or at least one waste bag (5). In use case, the cassette is operably coupled with the cycler. The system may comprise a pumping mechanism (7), at least one sensor (8), a display device (10) (which may be a touch screen) and other means (9), for example input means. The pumping mechanism and/or at least one sensor may be operably coupled to specific area of the cassette. Said system may comprise a mathematical model (11) as described hereafter. All of these elements may be connected to, and/or used and/or controlled by a processor (6).

Figure 2:
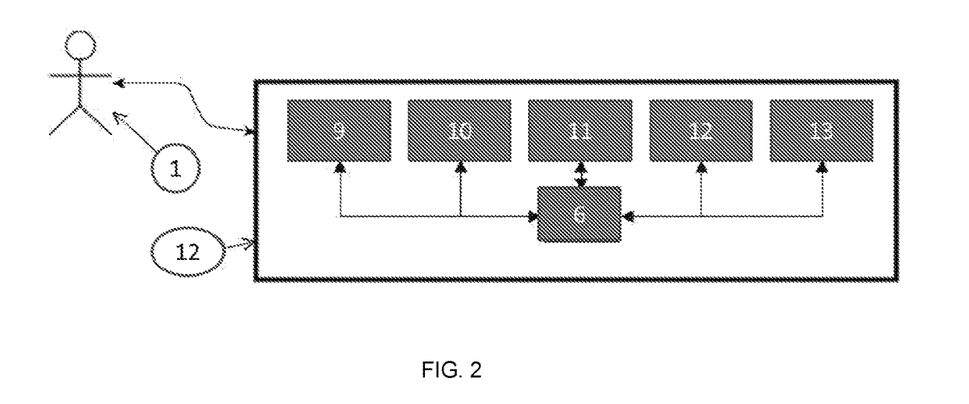
FIG. 2 illustrates a system without cycler

In another embodiment as disclosed by the FIG. 2, the system does not comprise a cycler but comprises a display device (10) (for example a touch screen), inputs means (9, 12) (for example: keypad, mouse, button . . . ), a mathematical model (11), a processor (6) and other means (13). In this case, the system may comprise a computer device like a personal computer, a laptop, . . . .

The display device (10) may display several screens by which the system informs the user of the treatment parameters and by which the user may enter or change at least one parameter.

Some medical treatments require to be applied in a sequential manner. Thus, a medical treatment may comprise a treatment sequence having one or several cycle sets which may be repeated. Furthermore, said cycle set may comprise a first phase followed by a second phase. Thus, a treatment may comprise:
- only one cycle set, thus the treatment comprises a single type of cycles which may be repeated a determined number of times.
- Several cycle sets, thus the treatment comprises several distinct sets of cycles and each cycle set comprises a type of cycle which may be repeated a determined number of times.

In case of a dialysis treatment, a dialysis treatment may comprise one or several cycles, in particular in case of automated peritoneal dialysis therapy (APD). Preferentially, said cycle comprises a fill phase and a dwell phase. Furthermore, the cycle may comprise a drain phase. An APD may comprise a cycle set in which each cycle may be substantially similar and may comprise three distinct phases (fill, dwell, drain). Thus, a cycle set may comprise a determined number of similar cycles. An APD may further comprise several cycle sets wherein each cycle set is substantially different.

APD therapy may be:
A Continuous Cycling Peritoneal Dialysis (CCPD). The CCPD is one popular APD therapy because it performs a full drain after every dwell, minimizing the potential for overfill due to the fluid that is ultrafiltered from the patient's body.
A Tidal. The Tidal is another popular APD Therapy in which the drain is voluntarily partial. Thus, to prevent an overfill of the peritoneal cavity, the subsequent fill has to be reduced.

In one embodiment, a cycle set may comprise at the end of the treatment a specific drain. In particular, when the cycle set is set up to perform a Tidal Therapy, the drain of each cycle of the cycle set is partial but the last drain may be a full drain.

In this document, the parameters of the treatment may be changed by a user, preferentially a caregiver. But the caregiver should not need a specific training to use the system in particular to program the parameter of the treatment. Said parameter may be: the volume of dialysate infused during a fill phase of a cycle and/or the number of the cycle included in the cycle set and/or the percentage of the dialysate drained during a drain phase of a cycle and/or the duration of the cycle set and/or the dwell time of a dwell phase of a cycle and/or the total volume of dialysate infused during the cycle set.

In one embodiment, the user does not have to determine a specific drain mode of the cycle set (tidal mode, full drain mode, . . . ), the user can change the percentage of drain so as to have a tidal treatment or full drain or no drain. Unlike the machine of the art which prompts to select a tidal mode or a full drain mode before to enter the other parameters. Thus, the user sequentially enters the parameters of the treatment and it is complex or impossible to change a previous parameter. Furthermore, when the user enters the next parameters, the user cannot change the drain mode (tidal or full drain mode). While thanks to the intuitive setting of the invention, the user can change the drain mode even if the user enters other parameters.

In one embodiment, the system of the invention comprises a graphical user interface (GUI) for a dialysis system. Said GUI comprises a display device (10) and an electronic processor (6) that operates with the display device to display a plurality of screens.

Figure 3:
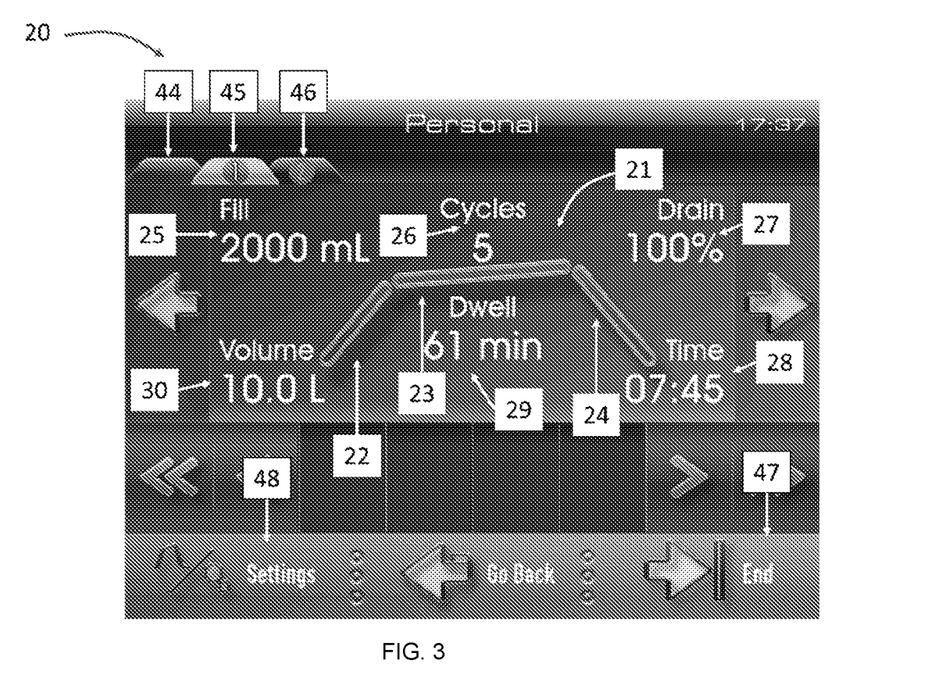
FIGS. 3, 4 and 6 show three cycle set programming screens

As shown by the FIG. 3, one of said screens is a cycle set programming screen (20) by which a user can program a cycle set comprising a type of cycle which may be repeated a determined numbers of times. Said type of cycle includes a fill phase (22), a dwell phase (23) and an optional drain phase (24). In one embodiment, the user may program at least one cycle set comprising at least one cycle for a treatment. In one embodiment, a cycle set may comprise only one fill phase. This type of cycle set may be the last cycle set of a treatment sequence.

The cycle set programming screen (shown by the FIG. 3) displays a set of adjustable and/or modifiable parameters (25, 26, 27, 28, 29, 30, . . . ) employed by the dialysis system in a dialysis treatment. Thanks to the intuitive system of the invention, when one of said parameters (25, 26, 27, 28, 29, 30, . . . ) is changed by a user, the processor (6) automatically adjusts at least one other parameter (25, 26, 27, 28, 29, 30, . . . ).

In one embodiment, the system comprises at least one parameter which is modifiable by the user and adjustable by the processor. For example, the display device may display a first and second parameters, where the first parameter is modifiable (by the user) and adjustable (by the processor depending on the second parameter) and the second parameter is modifiable (by the user). If the user modifies the first parameter and then the second parameter, even if the user has modified the first parameter, the system will adjust the first parameter depending on the second parameter. This feature is important because, the system is adapted to customize the treatment as far as possible depending on the user's (or patient's) needs and constraints, and to comply with the treatment or with constraints of the system (for example the flow rate, the dwell time, the duration of the fill phase, the dialysate volume needs for the treatment, . . . ). For example, if the first parameter is the dialysate volume and the second parameter is the percentage of drain, the user can select a value for the first parameter (for example 3 L because the patient does not need more dialysate for her treatment) and then select the percentage of the drain (for example 80% which may be a requirement of the caregiver), the system will automatically adjust the first parameter depending on the second parameter (because a part of the previous fill is retained in the peritoneal cavity and thus the treatment need less dialysate). Thus the processor may use a mathematical model to adjust (automatically, without other action of the user) the first parameters, wherein the mathematical model takes into account the new value of the second parameter.

Furthermore, the second parameter may be also adjustable by the system. In this case, the first and the second parameters are modifiable and adjustable and said parameters may be interdependent. In the last case, the first parameter (respectively the second parameter) may be modified by the user and the first parameter (respectively the second parameter) may be adjusted by the processor (using a mathematical model) depending on the second parameter (respectively the first parameter).

Preferentially, the processor is programmed to adjust the parameters depending on a priority set by the user, the manufacturer or other. Said priority forces the processor to adjust a medical treatment parameter rather than another and/or defines the dependency between the medical treatment parameters. Said priority may be changed.

Figure 7:
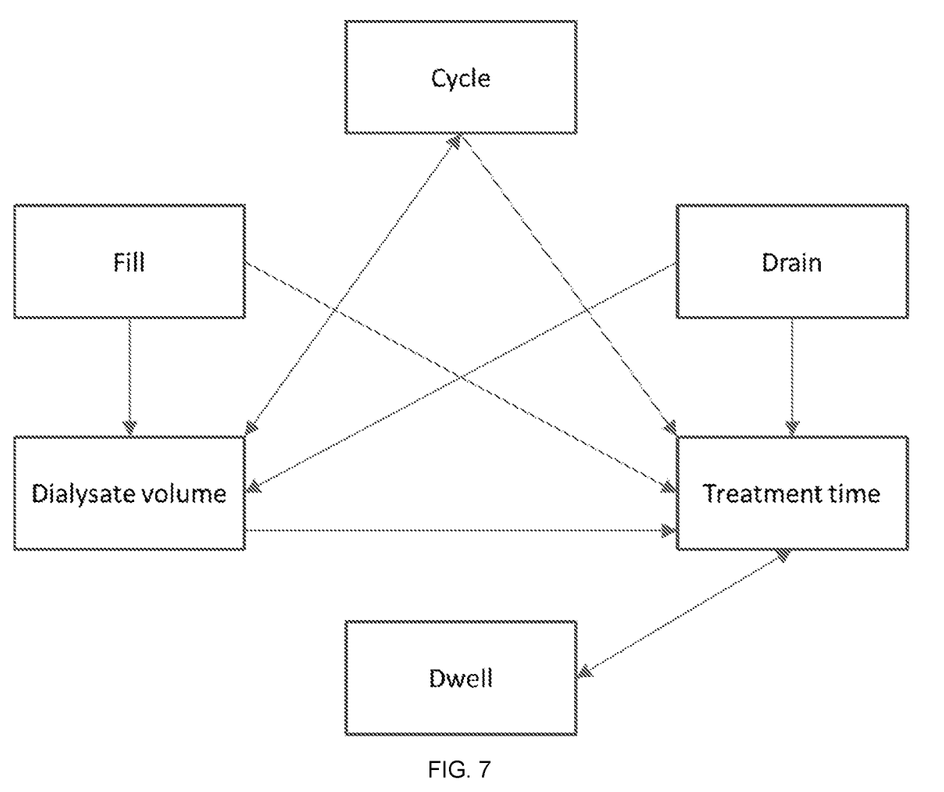
FIG. 7 shows the potential dependence between the parameters

An example of the dependence rules between the parameters is shown by the FIG. 7. In this example, all adjustable parameters are also modifiable by the user. For example, the fill parameter is modifiable by the user and a modification of the fill parameter may cause an adjustment of the dialysate volume parameter and/or the treatment time parameter. Other example, the Dwell parameter is depending on the treatment time parameter and vice versa.

In the example shown in the FIG. 7, the fill parameter may be the fill volume (volume of dialysate which is delivered to the patient at each fill phase, in case of CCPD), the cycle parameter may be the number of cycle repetition, the drain parameter may be the percentage of the drain, the treatment time may be the time of the full treatment or the time of the selected cycle set, the dwell parameter may be the dwell time, the dialysate volume parameter may be the dialysate need for the selected cycle set.

In one embodiment, the mathematical model used by the processor may take into account at least one of the following rules:
the number of the cycle included in the cycle set depends on the total volume of dialysate infused during the cycle set; and/or
the duration of the cycle set depends on the volume of dialysate infused during a fill phase of a cycle and/or the number of cycles included in the cycle set and/or the percentage of the dialysate drained during a drain phase of a cycle and/or the dwell time of a dwell phase of a cycle and/or the total volume of dialysate infused during the cycle set; and/or
the total volume of dialysate infused during the cycle set depends on the volume of dialysate infused during a fill phase of a cycle and/or the number of cycles included in the cycle set and/or the percentage of the dialysate drained during a drain phase of a cycle; and/or the dwell time of a dwell phase of a cycle depends on the duration of the cycle set.

Preferentially, when the user changes:
the volume of dialysate infused during a fill phase of a cycle, the processor may adjust the total volume of dialysate infused during the cycle set and/or the duration of the cycle set; and/or
the total volume of dialysate infused during the cycle set, the processor may adjust number of cycles included in the cycle set and/or the duration of the cycle set; Advantageously, the increment of said total volume depends on the volume of dialysate infused during a fill phase of a cycle. And/or
the number of cycles included in the cycle set, the processor may adjust the total volume of dialysate infused during the cycle set and/or the duration of the cycle set; and/or
the percentage of the dialysate drained during a drain phase of a cycle, the processor may adjust the total volume of dialysate infused during the cycle set and/or the duration of the cycle set; and/or
the dwell time of a dwell phase of a cycle, the processor may adjust the duration of the cycle set; and/or
the duration of the cycle set, the processor may adjust dwell time of a dwell phase of a cycle.

Figure 6:
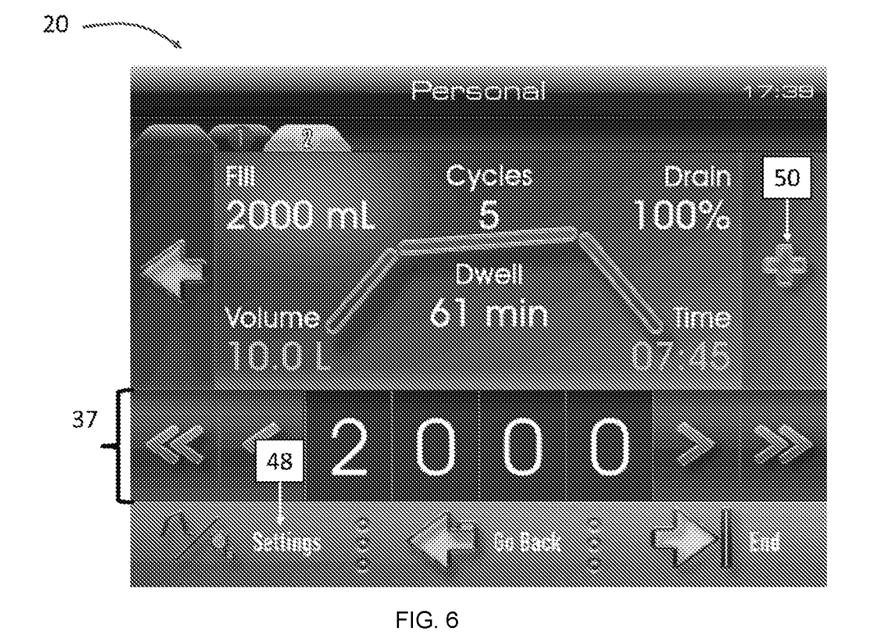

In one embodiment (FIG. 6), if the user wants to change or enter a treatment parameter, then the user selects or touches the corresponding area. A specific area (37) may be dedicated for displaying of the parameter and optional input means (digital button on the screen, for example arrows). The selected parameter may be highlighted (see the parameter "Fill").

In one embodiment, the user cannot enter a non-acceptable value. Indeed, the system (via for example a mathematical model) may limit the values of parameters. Thus, the parameter may be modified and/or adjusted taking into account of an range of permitted values (acceptable for the patient, the treatment, . . . ). This range of permitted values may be:
predetermined by the caregiver or the manufactor, . . . for example: Min of the fill parameter may be 500 mL (or 100 mL) and Max of the fill parameter may be 2.5 L (or 7 L); or
limited according to another parameter(s). For example, the Min and/or the Max of time treatment parameter may be limited by the value(s) of the fill and/or drain and/or dwell and/or cycle parameters (for example the time required for the dialysate infusion). Other example, the treatment duration parameter for the selected cycle set may be limited by the total duration of the treatment which may be predetermined by the caregiver or the manufactor, . . . .

Thus, the system may compute (automatically) a range of permitted values for a first parameter and may change the range (compute a new range depending on the second parameter) when a second parameter is modified or adjusted.

Figure 8:
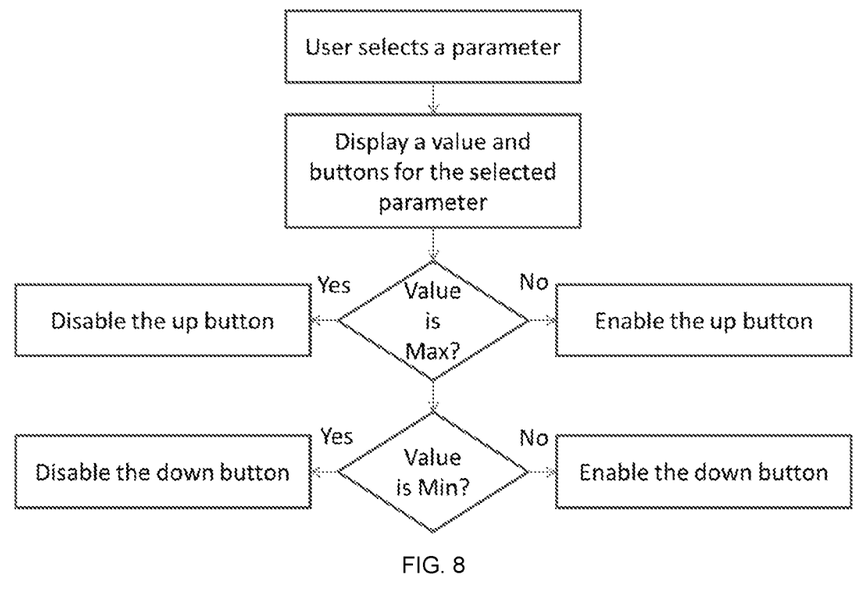
FIG. 8 shows a flowchart of the button activation.

In one embodiment, as disclosed by the FIG. 8, the input means (the button) used by the user are enable or disable according to the range of permitted value.

In one embodiment, the cycle set programming screen may graphically illustrate a full cycle (21) comprising a fill phase (22), a dwell phase (23) and optionally a drain phase (24). As disclosed by the FIG. 4, the cycle set programming screen (20) may comprise three distinct areas which graphically illustrates a full cycle:
a first area (31) dedicated to the parameters of the fill phase,
a second area (32) dedicated to the parameters of the dwell phase,
a third area (33) dedicated to the parameters of the optional drain phase.

Figure 4:
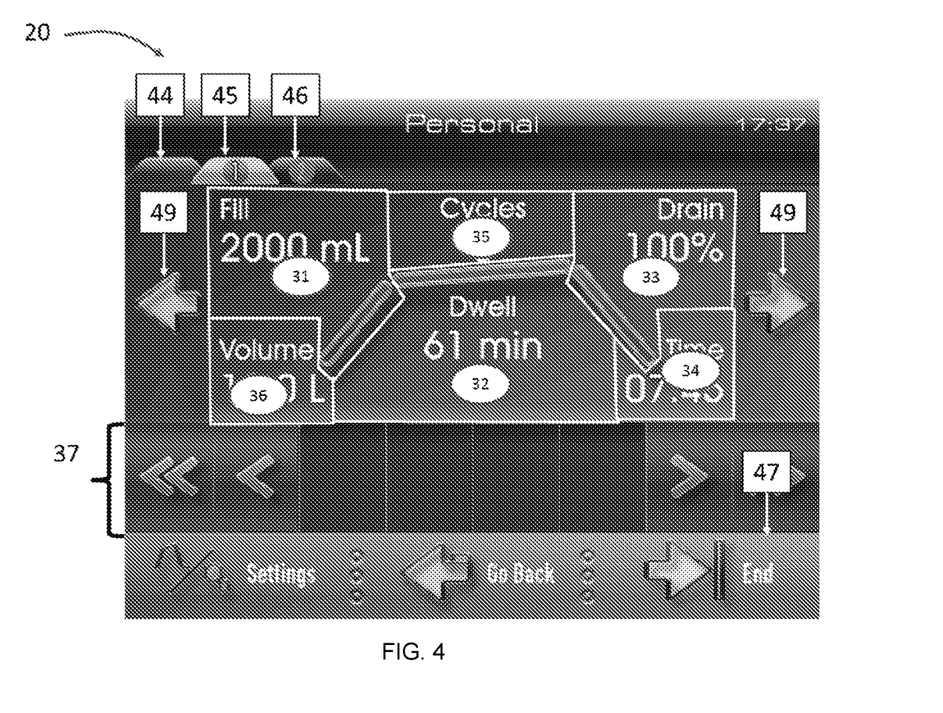

In one embodiment, cycle set programming screen (20) further comprises at least one additional distinct area (34, 35, 36) dedicated to other parameters of the cycle set which may be the number of cycles included in the cycle set (35) and/or the duration of the cycle set (34) and/or the total volume of dialysate infused during the cycle set (36).

Thanks to this screen, the user can see with only one screen the most important parameters of the peritoneal dialysis cycle.

Figure 5A:
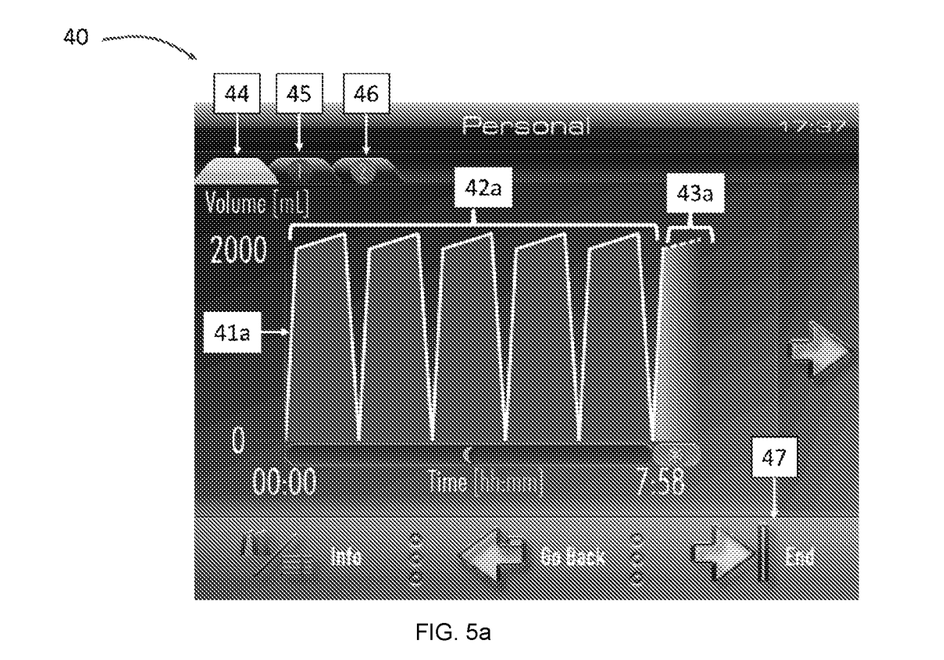
FIGS. 5a and 5b shows a full treatment screen (the overview screen)
Figure 5B:
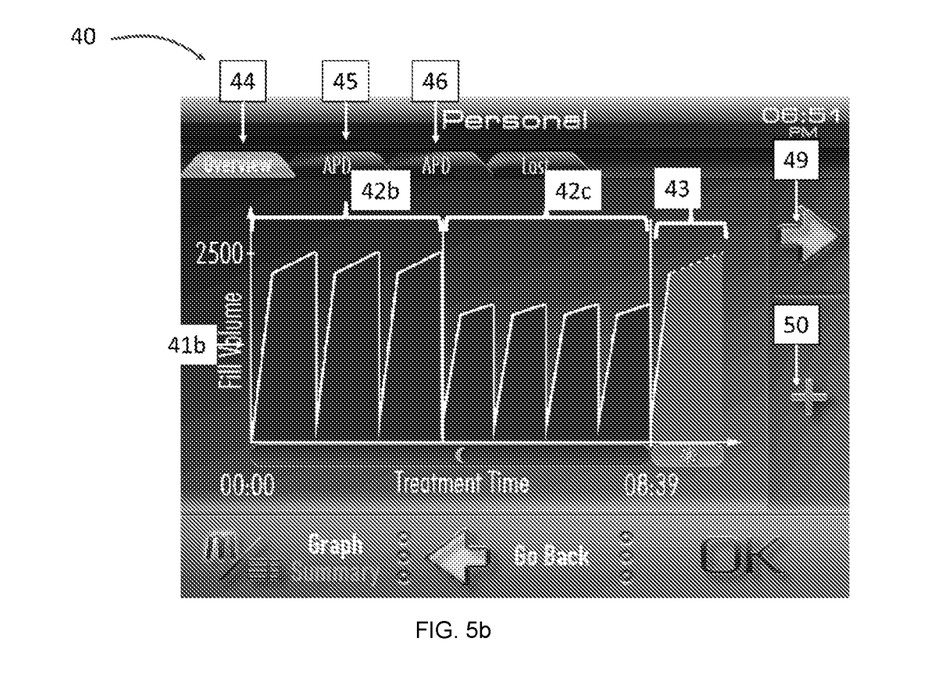

Furthermore, the display device (10) may display a full treatment screen (40) (the "overview" screen) as shown by the FIGS. 5a and b. This screen graphically illustrates a full treatment comprising one or more cycle sets. For example, the full treatment screen shown in the FIG. 5a comprises two distinct cycle set (42a, 43a) in which the first cycle set (42a) includes a cycle (41) which is repeated five times and the second cycle set (43a) has only one cycle (said cycle does not have a drain phase). A specific colour may be assigned to each cycle set, for example the first cycle set has a red indicator and the second cycle set has a yellow indicator. The FIG. 5b is another overview screen (40) which displays the full treatment comprising three distinct cycle sets (42b, 42c, 43b). The first cycle set (42b) comprises one cycle type (41b) repeated 3 times. In the FIG. 5b, the cycle sets are separated by a vertical straight line. Furthermore, the colour may be similar for each type of treatment, for example, red for APD classic, green for the last fill, orange for a Tidal, . . . . In one embodiment, the user can select the cycle set (so as to display the programming screen of the selected cycle set) by touching the cycle set in the overview screen.

The user can select, activate or touch a cycle set (42, 43) displayed by the full treatment screen (40) so that the cycle set programming screen (20) of said cycle set is displayed on the display device.

Optionally, the full treatment screen and/or the cycle set programming screen comprise tabs (44, 45, 46) allowing the user to select a specific screen to display. For example, if the user selects, activates, touches:
the first tab (44), the display device displays the full treatment screen (the overview screen)
the second tab (45), the display device displays a first cycle set programming screen.
the third tab (46), the display device displays a second cycle set programming screen.

When a tab is selected or displays the corresponding screen, this tab may be highlighted. In the tabs, an identification means may be displayed, for example a number or text which depicts the type of cycle or the number of cycle set.

The tab may comprise the same indicator as the cycle set, for example, the tab may have the same colour of the corresponding cycle set or type of cycle (APD, Last, APDC, . . . ). The display device may use other distinction means such as digital, shape, . . . .

The full treatment screen and/or the cycle set programming screen comprise a validation icon (47) adapted to display a specific other screen. In one embodiment, the validation icon allows the user to validate all of parameters. Unlike the system of the art where the user has to validate each setting steps.

In one embodiment, these screens may also comprise a specific area displaying treatment identification. For example the name of the treatment is "personal" which may be change by the user.

The modifiable parameters (25, 26, 27, 28, 29, 30, . . . ) may be the volume of dialysate infused during a fill phase of a cycle (25) and/or the number of cycles included in the cycle set (26) and/or the percentage of the dialysate drained during a drain phase of a cycle (27) and/or the duration of the cycle set (28) and/or the dwell time of a dwell phase of a cycle (29) and/or the total volume of dialysate infused during the cycle set (30). The adjustable parameters may be may be the volume of dialysate infused during the number of cycles included in the cycle set (26) and/or the duration of the cycle set (28) and/or the dwell time of a dwell phase of a cycle (29) and/or the total volume of dialysate infused during the cycle set (30). In one embodiment, the user can change at least one of said parameters and the cycle set programming screen may allow programming all of said parameters within only one screen.

In one embodiment, the percentage of the dialysate drained during a drain phase of a cycle (27) allows performing a tidal therapy or full drain or no drain. Thus, if said percentage is 100%, the system will perform a CCPD (a full drain at each cycle of the cycle set). If the percentage is comprised between 1% and 99%, the system will perform a tidal therapy and the last drain may be a full drain. If the percentage is 0%, the system will not perform any drain. Thus, in compare to the prior art device, the invention allows determining the type of therapy without any additional screen. For example, if the user wants to program a tidal therapy, the user selects a percentage comprised between 1% and 99%. If the user wants to program a Continuous Cycling Peritoneal Dialysis ("CCPD") therapy, the user selects a 100% drain. While the prior art devices display a specific screen and the user has to select between different therapies (Tidal, CCPD, . . . ) before to program the treatment parameters.

Figure 9A:
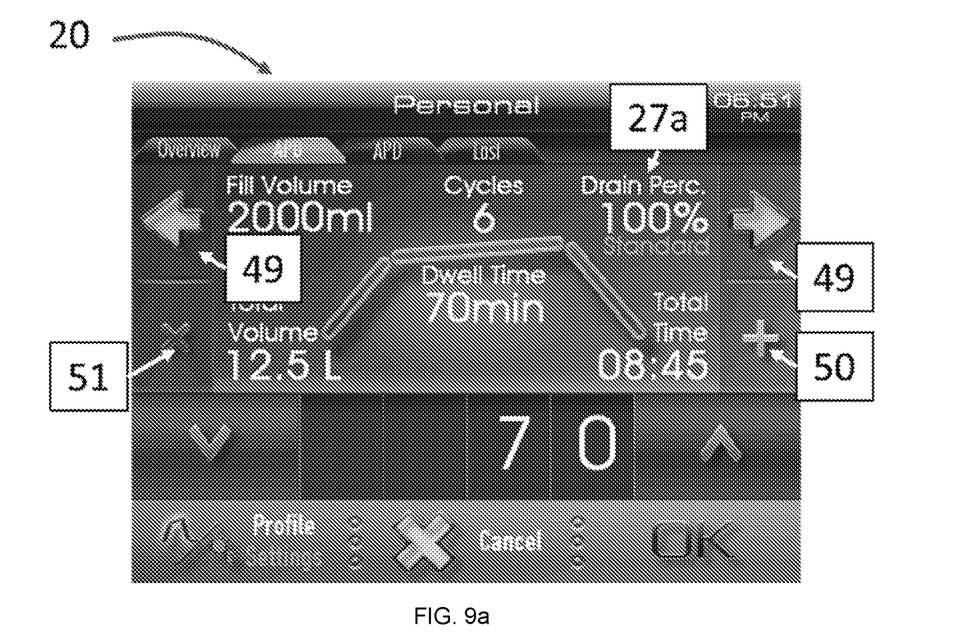
FIGS. 9a, 9b, 10a and 10b show other possible cycle set programming screen.
Figure 9B:
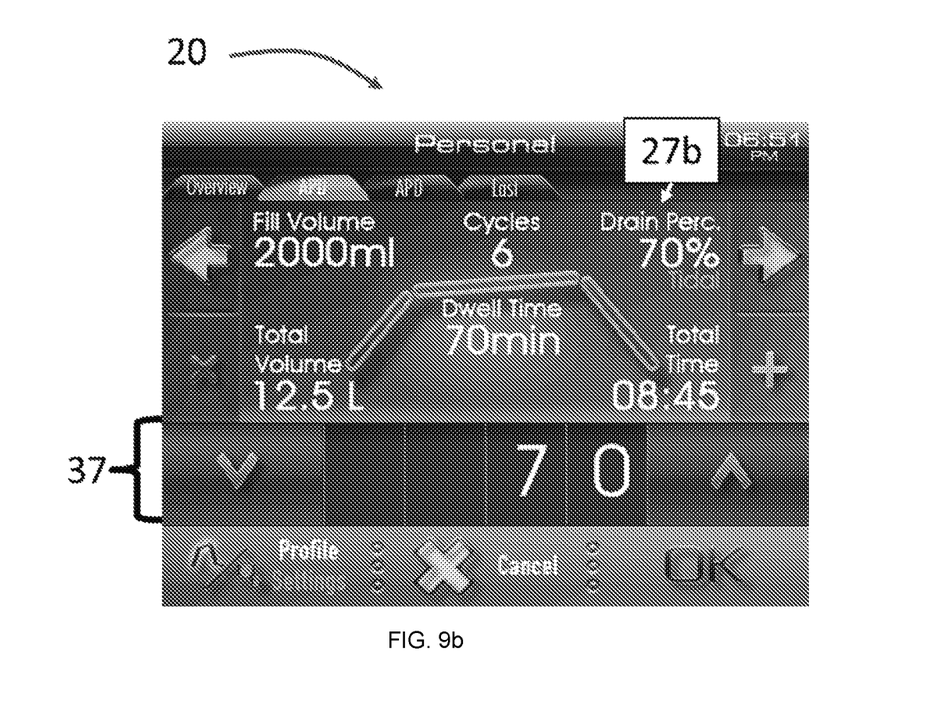
Figure 10A:
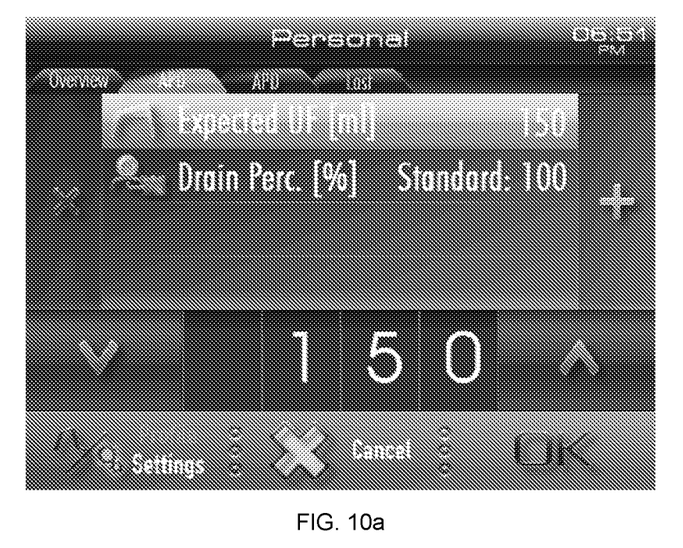
Figure 10B:
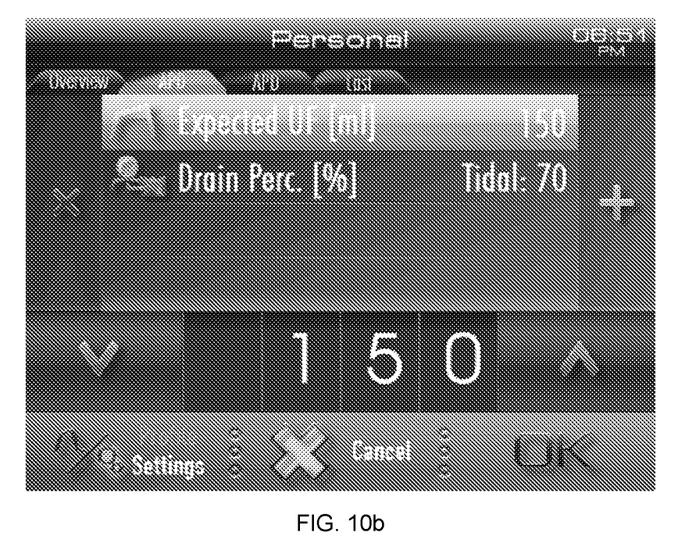

According to one embodiment, the FIG. 9a shows a standard drain (100%) and the FIG. 9b shows a Tidal (70%), this identification (standard or Tidal) of the treatment may be automatically display according to the percentage of the drain (which may be entered and/or modified by the user). This parameter may be displayed in other screen, for example on a setting screen shows by the FIG. 10a or 10b. In this case, this parameter may be not displayed on the cycle set programming screen which graphically illustrates the treatment. The FIGS. 10a and 10b show a setting screen by which the user can enter or modify parameters, for example the expected UF, or the modifiable parameters cited above. A similar dependence rules may be used.

The cycle set programming screen displays a setting icon (48) which allows the user to program other parameters, for instance: the dialysate type, the glucose concentration of the dialysate, the dialysate fluid concentration and/or the break-point operating mode.

In one embodiment, the cycle set programming screen (or the medical system) comprises at least one button (49) which may depict an arrow for navigating in-between tabs/ cycle sets programming screen. Thanks to this button, the user can (by pressing on) reach a subsequent or previous cycle set of the treatment sequence. An add button (50) may be pressed (for example displayed on a programming screen or arranged on the medical system) so as to add a new cycle set. In one embodiment, the add button is displayed on the overview screen so as to create a first cycle set or to add a cycle set before all the existing ones. In one embodiment, the system may ask to the user (by displaying a specific or popup window) where the user wants to add in the treatment sequence. Furthermore, the medical system or a cycle set programming screen may comprise a delete button (51) which may be used to delete a treatment sequence (full or partial) or a cycle set (for example the cycle set which is selected or displayed).

According to one preferred embodiment, the invention describes a medical system for setting a medical treatment, which comprises:
a display device which comprises a graphical user interface. Preferentially, the graphical user interface is configured to display a first and a second parameter related to the medical treatment, and
a computing device which is operatively coupled to the display device.
Preferentially, the computing device is configured to:
display on the graphical user interface the first and the second parameters
allow a user to modify the value of the first and the second parameter; and
when the value of the first parameter has been modified by the user, adjust the value of the second parameter and vice-versa.

The display device may comprise input means by which the user modifies the value of parameters. The graphical user interface may be configured to display a third parameter, and when the user modifies the value of the third parameter, the computing device may be configured to adjust the value of the first and/or the second parameters. The computing device may use a mathematical model which may define the dependence between the parameters. The graphical user interface may be configured to graphically illustrate the medical treatment. The graphical user interface may be configured to display a cycle set of the medical treatment.

In one embodiment, the first, second or third parameter may be one of the following parameters: a volume of dialysate, a number of cycles, a percentage of the dialysate volume, the duration of the treatment or a dwell time. The cycle set may comprise a fill phase, optionally a dwell phase and optionally a drain phase.

Preferentially, the graphical user interface may be configured to display on the display device a plurality of stacked windows, wherein each window has a corresponding tab that is displayed on the user interface adjacent the tabs of the other windows, each tab being selectable to bring the window corresponding to that tab to a top of the stack as an active window in which a user can view and/or edit parameters of medical treatment while the windows corresponding to the other tabs remain in the background.

The medical treatment may comprise at least two distinct cycle sets and wherein each cycle set is displayed on a specific window. The system or the programming screen may further comprise a (e.g. virtual) button which allows:
  reaching a subsequent or previous cycle set in a treatment sequence, or
  adding a window which displays a new cycle set, or
  deleting a determined cycle set.

Preferentially, one of the windows may display a global view of the medical treatment or treatment sequence.

The computing device may be configured to compute a range of permitted values for at least one of parameters. The graphical user interface may be configured to display on the display device a setting screen comprising three distinct areas:
  a first area configured to depict a modifiable parameter related to the fill phase, the dwell phase or the drain phase,
  a second area configured to depict a modifiable parameter dedicated to the number of cycles, and
  a third area configured to depict a modifiable parameter dedicated to a dialysate volume or a duration of the treatment

The invention claimed is:

1. A medical system for controlling a peritoneal dialysis treatment, the peritoneal dialysis treatment having cycles including at least one of a fill phase, a dwell phase, and a drain phase, the system comprising:
  a display device configured to display a graphical user interface, the graphical user interface configured to display a first parameter and a second parameter related to the peritoneal dialysis treatment; and
  a computing device operatively coupled to the display device, the computing device configured to
    display a setting screen on the graphical user interface with the first and the second parameters, the first and second parameters that are simultaneously displayed on the same setting screen, the first and second parameters being user-modifiable parameters, the first parameter including a number of cycles of the fill phase, and the second parameter including at least one of a dialysate volume and a duration of the peritoneal dialysis treatment,
    allow a user to modify a value of the first parameter and a value of the second parameter,
    adjust the value of the second parameter based on the modified value of the first parameter, upon modification of the first parameter by the user, or adjust the value of the first parameter based on the modified value of the second parameter, upon modification of the second parameter by the user, and
    display on the same setting screen of the graphical user interface the modified first parameter and the adjusted second parameter or the modified second parameter and the adjusted first parameter.

2. The system according to claim 1, wherein the display device comprises an input device configured to allow the user to modify the value of first parameter and the value of the second parameter.

3. The system according to claim 1, wherein the graphical user interface is further configured to display a third parameter, the third parameter including a percentage of dialysate drained by the drain phase,
  wherein when the user modifies a value of the third parameter, the computing device is configured to adjust at least one of the value of the first parameter and the value of the second parameter based on the modified value of the third parameter, and is configured to display on the same setting screen of the graphical user interface the modified third parameter and at least one of the adjusted first and the adjusted second parameters.

4. The system according to claim 1, wherein the computing device is further configured to
  use a mathematical model defining a dependence between the first parameter and the second parameter to adjust the value of the second parameter based on the modified value of the first parameter, or to adjust the value of the first parameter based on the modified value of the second parameter.

5. The system according to claim 1, wherein the graphical user interface is configured to display a plurality of stacked windows,
  wherein each window of the plurality of stacked windows has a tab that is displayed on the graphical user interface adjacent to tabs of each of the other windows of the plurality of stacked windows, each tab being selectable to bring the window corresponding to the selectable tab to a top of a stack as an active window, the active window configured to allow the user to at least one of view and edit parameters of the peritoneal dialysis treatment while the other windows remain in a background.

6. The system according to claim 1, wherein the peritoneal dialysis treatment comprises at least two distinct cycle sets, each cycle set of the at least two distinct cycle sets is displayed on a specific window of the graphical user interface.

7. The system according to claim 1, the system further comprising a button configured to perform at least one of
  reach a subsequent or a previous cycle set in a treatment sequence of the peritoneal dialysis treatment,
  adding a new cycle set, and
  deleting a determined cycle set.

8. The system according to claim 1, wherein a window of the plurality of stacked windows displays a global view of the peritoneal dialysis treatment.

9. The system according to claim 1, wherein the computing device is configured to compute a range of permitted values for at least one of the first and second parameters.

10. The system according to claim 3, wherein the setting screen including three distinct areas, the three distinct areas including:
  a first area configured to depict the first modifiable parameter,
  a second area configured to depict the second modifiable parameter, and a third area configured to depict the third modifiable parameter.

11. The system according to claim 1, wherein the first parameter further includes a percentage of the dialysate drained during the drain phase of a cycle, and when the first parameter is modified to be between 1% and 99%, the computing device is configured to automatically instruct a tidal therapy for the peritoneal dialysis treatment or perform a partial drain at each cycle of a cycle set.

12. The system according to claim 1, wherein the first parameter further includes a percentage of the dialysate drained during the drain phase of a cycle, and when the first parameter is substantially equal to 100%, the computing device is configured to automatically instruct a Continuous Cycling Peritoneal Dialysis (CCPD) or perform a full drain at each cycle of a cycle set.

13. The system according to claim 1, wherein the displaying of the modified first parameter and the adjusted second parameter or the modified second parameter and the adjusted first parameter on the same setting screen is performed while the user is modifying the first parameter or the second parameter.

14. The system according to claim 3, wherein after the adjusting by the computer device, the computing device is configured to further allow the user to select and to modify at least one of the first user-modifiable parameter, the second user-modifiable parameter, and the third user-modifiable parameter on the setting screen.

15. The system according to claim 1, wherein the computing device is further configured to permit a modification to one of the user-modifiable parameters within a range of permitted values, the range of permitted values depending on a value of another one of the user modifiable parameters.

16. A method for displaying information related to a peritoneal dialysis treatment, the method being performed with a system for controlling the peritoneal dialysis treatment, the system including a display device for displaying a graphical user interface and a computing device, the method comprising the steps of:
displaying a setting screen on the graphical user interface with a first parameter and a second parameter, the first and second parameters that are simultaneously displayed on the same setting screen, the first and second parameters being user-modifiable parameters, the first parameter including a number of cycles of a fill phase of the peritoneal dialysis treatment, and the second parameter including at least one of a dialysate volume and a duration of the peritoneal dialysis treatment;
allowing a user to modify a value of the first parameter and a value of the second parameter;
adjusting the value of the second parameter based on the modified value of the first parameter, upon modification of the first parameter by the user, or adjust the value of the first parameter based on the modified value of the second parameter, upon modification of the second parameter by the user; and
displaying on the same setting screen of the graphical user interface the modified first parameter and the adjusted second parameter or the modified second parameter and the adjusted first parameter.

17. The method according to claim 16, further comprising a step of:
displaying on the graphical user interface a button configured to perform at least one of
reach a subsequent or a previous cycle set in a treatment sequence of the peritoneal dialysis treatment,
adding a new cycle set, and
deleting a determined cycle set.

18. The method according to claim 16, wherein the step of displaying displays a window of a plurality of stacked windows with a global view of the peritoneal dialysis treatment.

19. The method according to claim 16, wherein the first parameter further includes a percentage of the dialysate drained during the drain phase of a cycle, and the percentage is displayed as a numerical percentage value.

20. The method according to claim 16, wherein the first parameter further includes a percentage of the dialysate drained during the drain phase of the cycle, and when the first parameter is modified to be between 1% and 99%, the computing device is configured to automatically instruct a tidal therapy for the peritoneal dialysis treatment or perform a partial drain at each cycle of a cycle set.

21. The method according to claim 16, wherein the first parameter further includes a percentage of the dialysate drained during the drain phase of a cycle, and when the first parameter is substantially equal to 100%, the computing device is configured to automatically instruct a Continuous Cycling Peritoneal Dialysis (CCPD) or perform a full drain at each cycle of a cycle set.

22. The method according to claim 16, wherein the step of displaying the modified first parameter and the adjusted second parameter or the modified second parameter and the adjusted first parameter on the same setting screen is performed while the user is modifying the first parameter or the second parameter.

23. The method according to claim 16, further comprising the step of:
permitting a modification of one of the user-modifiable parameters within a range of permitted values, the range of permitted values depending on a value of another one of the user modifiable parameters.

24. A dialysis system for performing a peritoneal dialysis treatment comprising a cycle set including at least one of a fill phase, a dwell phase, and a drain phase, the system comprising:
a display device configured to display a graphical user interface, the graphical user interface configured to display a plurality of parameters on a setting screen, the setting screen including three distinct areas, the three distinct areas including,
a first area configured to show a first modifiable parameter, the first modifiable parameter including a number of cycles of the fill phase,
a second area configured to show a second modifiable parameter, the second modifiable parameter including a percentage of dialysate drained by the drain phase, and
a third area configured to show a third modifiable parameter, the third modifiable parameter including at least one of a dialysate volume and a duration of the peritoneal dialysis treatment,
a computing device operatively coupled to the display device, the computing device configured to,
display on the same setting screen of the graphical user interface values of the first, second, and third modifiable parameters,
allow a user to adjust at least one of the first, second, and third modifiable parameters that are simultaneously displayed on the same setting screen, and
display on the same setting screen of the graphical user interface the adjusted one of the first, second, and third modifiable parameters and the other ones of the first, second, and third parameters, upon the user adjusting one of the first, second, and third modifiable parameters.

25. The dialysis system according to claim 24, further comprising:
a button configured to perform at least one of
reach a subsequent or a previous cycle set in a treatment sequence of the peritoneal dialysis treatment,
adding a new cycle set, and
deleting a determined cycle set.

26. The dialysis system according to claim 24, wherein the display device is further configured to display on the graphical user interface a window showing a global view of the peritoneal dialysis treatment.

27. The system according to claim 24, wherein the second modifiable parameter is displayed as a numerical percentage value that represents the percentage of the dialysate drained during the drain phase of a cycle.

28. The system according to claim 24, wherein when the second modifiable parameter is modified to be between 1% and 99%, the computing device is configured to automatically instruct a tidal therapy for the peritoneal dialysis treatment or perform a partial drain at each cycle of the cycle set.

29. The system according to claim 24, wherein when the second modifiable parameter is substantially equal to 100%, the computing device is configured to automatically instruct a Continuous Cycling Peritoneal Dialysis (CCPD) or perform a full drain at each cycle of the cycle set.

30. The system according to claim 24, wherein the display of the adjusted one of the first, second, and third modifiable parameters on the same setting screen is performed while one of the first, second, and third modifiable parameters is adjusted by the user.

31. The dialysis system of claim 24, wherein the computing device is further configured to permit a modification of one of the user-modifiable parameters within a range of permitted values, the range of permitted values depending on a value of another one of the user modifiable parameters.

* * * * *